United States Patent
Carlin et al.

(10) Patent No.: US 9,625,334 B2
(45) Date of Patent: Apr. 18, 2017

(54) METHOD OF MEASURING ELONGATION OF A FASTENER WITH ULTRASOUND, PERFORMED BY A POWER TOOL, AND A POWER TOOL

(71) Applicant: ATLAS COPCO INDUSTRIAL TECHNIQUE AB, Stockholm (SE)

(72) Inventors: Carl-Gustaf Carlin, Tyresö (SE); Erik Vilhelm Persson, Solna (SE); Jarl-Olof Hulden, Solna (SE)

(73) Assignee: ATLAS COPCO INDUSTRIAL TECHNIQUE AB, Stockholm (SE)

( * ) Notice: Subject to any disclaimer, the term of this patent is extended or adjusted under 35 U.S.C. 154(b) by 0 days.

(21) Appl. No.: 14/897,637

(22) PCT Filed: Jun. 9, 2014

(86) PCT No.: PCT/EP2014/061936
§ 371 (c)(1),
(2) Date: Dec. 10, 2015

(87) PCT Pub. No.: WO2014/198680
PCT Pub. Date: Dec. 18, 2014

(65) Prior Publication Data
US 2016/0138986 A1 May 19, 2016

(30) Foreign Application Priority Data
Jun. 12, 2013 (SE) ........................................ 1350717

(51) Int. Cl.
*F16B 31/02* (2006.01)
*G01L 5/24* (2006.01)
(Continued)

(52) U.S. Cl.
CPC .............. *G01L 5/246* (2013.01); *B25B 23/14* (2013.01); *G01N 29/07* (2013.01); *G01N 2291/02854* (2013.01)

(58) Field of Classification Search
CPC .......... G01L 5/246; G01N 2291/02854; G01N 2291/2691; G01N 29/07; G01N 29/343; A61N 7/00; B25B 23/14
(Continued)

(56) References Cited

U.S. PATENT DOCUMENTS 3,856,985 A * 12/1974 Yokoi ................. G01S 7/52071
348/163
4,602,511 A * 7/1986 Holt ....................... G01N 29/07
73/581
(Continued)

FOREIGN PATENT DOCUMENTS

SE            533385 C2      9/2010
WO      2010110716 A1    9/2010

OTHER PUBLICATIONS

Cohen M.N., et al., "Minimum peak sidelobes pulse compression codes", Proceedings of the IEEE International Radar Conference, Arlington, VA, May 1990, pp. 633-638.
International Search Report (ISR) dated Oct. 28, 2014 issued in International Application No. PCT/EP2014/061936.
Leukhin A.N., et al., "Binary Sequences With Minimum Peak Sidelobe Level Up to Length 68".

*Primary Examiner* — Max Noori
(74) *Attorney, Agent, or Firm* — Holtz, Holtz & Volek PC (57) ABSTRACT

The invention relates to a method of measuring elongation of a fastener by means of minimum peak side lobe (MPS) coded ultrasonic signals, and a power tool configured to performing the method. MPS coded signals with different base frequencies are transmitted into the fastener and a corresponding set of reflected signals are received from the fastener. Each reflected signal is cross-correlated with the corresponding transmitted signal, and a quality attribute of each transmitted signal is determined from the cross-corre-
(Continued)

lated signals. Based on the quality attributes at least one parameter of an ultrasonic measurement signal is determined and the measurement is performed by transmitting the ultrasonic measurement signal into the fastener, and receiving a reflected ultrasonic measurement signal.

20 Claims, 5 Drawing Sheets

(51) Int. Cl.
    *B25B 23/14*     (2006.01)
    *G01N 29/07*     (2006.01)

(58) Field of Classification Search
    USPC .................................... 73/761, 801, 862.21
    See application file for complete search history.

(56) References Cited

U.S. PATENT DOCUMENTS

| | | | |
|---|---|---|---|
| 5,970,798 A | 10/1999 | Gleman et al. | |
| 6,415,665 B1* | 7/2002 | Gilmore | B29C 47/92 425/169 |
| 2010/0154183 A1* | 6/2010 | Kibblewhite | F16B 25/10 29/25.35 |
| 2012/0017686 A1* | 1/2012 | Carlin | G01L 5/246 73/644 |
| 2015/0260592 A1* | 9/2015 | George | B25B 23/1425 73/629 |
| 2016/0069838 A1* | 3/2016 | Bueno | G01N 29/043 73/628 |

* cited by examiner

METHOD OF MEASURING ELONGATION OF A FASTENER WITH ULTRASOUND, PERFORMED BY A POWER TOOL, AND A POWER TOOL

The invention relates to a method of measuring elongation of a fastener with ultrasound, performed by a power tool in acoustic contact with the fastener. The invention further relates to a power tool comprising a tool head for engaging with a fastener, an ultrasonic transducer unit for transmitting ultrasonic signals into the fastener and receiving reflected ultrasonic signals from the fastener.

BACKGROUND

Power tools may be used in various assembly processes, including fastening of joints etc. When fastening joints it is important that fasteners of such joints are tightened such that required tightening force levels are reached.

In order to control the tightening force of joints, the elongation of the fastener may be monitored during fastening. A previous patent SE 533385 discloses a method and a tool for measuring elongation of a fastener with ultrasound. By measuring the elongation of the fastener, the tightening force of the fastener may be assessed.

However, there is always a need for improving such methods of measuring fasteners with ultrasound to be able to improve reliability and robustness of the measurements on elongation and thereby the reliability and robustness of measurements of the tightening force.

SUMMARY OF THE INVENTION

An object of the invention is thus to provide improvements in measuring elongation of a fastener with ultrasound using a power tool. Particularly it is an object to improve the reliability and robustness of the measurements on elongation.

Hence, the invention relates to a method of measuring elongation of a fastener with ultrasound, performed by a power tool in acoustic contact with the fastener. The method comprises:
 transmitting a set of primary minimum peak side lobe (MPS) coded ultrasonic signals with different base frequencies into the fastener,
 receiving a corresponding set of reflected primary ultrasonic signals from the fastener,
 cross-correlating each reflected primary ultrasonic signal with the corresponding transmitted primary ultrasonic signal, thus obtaining a set of primary cross-correlated signals,
 determining a quality attribute of each transmitted primary signal from the set of primary cross-correlated signals,
 determining at least one parameter of an ultrasonic measurement signal, for performing measurements of the fastener, based on the quality attributes of the set of transmitted primary signals,
 transmitting the ultrasonic measurement signal into the fastener,
 receiving a reflected ultrasonic measurement signal from the fastener, and
 measuring the elongation of the fastener based on the reflected ultrasonic measurement signal.

By transmitting minimum peak side lobe (MPS) coded ultrasonic signals into the fastener and cross-correlating reflected and transmitted ultrasonic signals, a much better correlation may be achieved as compared to other types of signals, e.g. conventional sine bursts. The correlation between the reflected and transmitted ultrasonic signals may be used to track a phase change of the ultrasonic signal during elongation, e.g. tightening of a threaded fastener. By improving the correlation, a measurement of the phase change, and thus the elongation, may be made more reliable and robust. Thus the use of minimum peak side lobe (MPS) coded ultrasonic signals may result in a more reliable and robust measurement of elongation of a fastener. The measurement of elongation of a fastener with a power tool may therefore be improved.

To obtain a MPS coded ultrasonic signal, selected periods of an ultrasonic signal to be modulated by a MPS code are phase shifted according to the MPS code.

MPS codes are binary sequences with low autocorrelation sidelobe levels which have been identified with sequence lengths (periods of the modulated wave form) up to 48 (M. N. Cohen, M. R. Fox, J. M. Baden. Minimum peak sidelobes pulse compression codes, Proceedings of the IEEE International Radar Conference, Arlington, Va., May 1990, pp. 633-638), and more recently up to 68 (Binary sequences with minimum peak sidelobe level up to length 68, A. N. Leukhin, E. N. Potehin, http://arxiv.org/ftp/arxiv/papers/1212/1212.4930.pdf).

By transmitting a set of primary minimum peak side lobe (MPS) coded ultrasonic signals with different base frequencies into the fastener, cross-correlating each reflected primary ultrasonic signal with the corresponding transmitted primary ultrasonic signal and determining a quality attribute of each signal of the set of transmitted primary signals using the cross-correlated signals, at least one parameter of the ultrasonic measurement signal may be selected such that the actual measurement may be made more reliable and robust. The at least one parameter may comprise the type of ultrasonic measurement signal or any other parameter of the ultrasonic measurement signal.

The MPS coded ultrasonic signals may be MPS coded ultrasonic sine signals. The ultrasonic signal modulated by the code may thus be a sinus signal or a sine burst. Thus phase information in the coded signal may be maintained.

The quality attribute of each signal of the set of transmitted primary signals may be based on attributes selected from the group consisting the following attributes, or combinations thereof:
 An amplitude of the cross-correlated signal. This relates to the total amplitude of the signal. Thus the total amplitude of the signal may be used as a quality attribute, to enhance the signal-to-noise ratio.
 A cross-correlation peak height. This relates to the peak height of the most prominent peak, i.e. a main peak, in the cross-correlated signal. Thus the absolute peak height of the most prominent correlation peak may be used as a quality attribute, to enhance the signal-to-noise ratio.
 A cross-correlation peak uniqueness. Different signal routes in the fastener may result in different time of flight of the signal and thus several correlation peaks. The cross-correlation peak uniqueness may relate to a ratio of peak height of a main peak to peak height of a secondary peak, e.g. the second most prominent peak in the cross-correlated signal. Thus the uniqueness of the most prominent peak with regard to other correlation peaks may be used as a quality attribute.
 A cross-correlation peak symmetry. This may relate to any measurement of symmetry of the main peak of the cross-correlated signal, e.g. symmetry of the left hand edge and the right hand edge. Overlapping correlation peaks corresponding to different signal routes in the fastener may result in asymmetric correlation peaks. By considering cross-correlation peak symmetry the risk of identifying overlapping correlation peaks etc. may be reduced.

An I/Q signal variance. Thus the method may include an assessment of the quality of a phase extraction from the received signal. If the variation (variance) of the I/Q signal in a given interval is low, the quality of the extracted phase in this interval is high, indicating that the quality of the received signal is high in the interval.

A difference between reflected signal phase and correlation peak position. The position of the correlation peak may be seen to indicate the time of flight of the signal in a number of periods of the base frequency of the signal. Any deviation from a complete number of periods, i.e. in parts of a period, may indicate a phase shift of the signal. This phase shift may be compared to the reflected signal phase to assess the quality of the signal.

The quality attribute may be based on a weighted sum of a plurality of attributes of the set of transmitted primary signals, selected from the group consisting of an amplitude of the cross-correlated signal, a cross-correlation peak height, a cross-correlation peak uniqueness, a cross-correlation peak symmetry, an I/Q signal variance, a difference between reflected signal phase and correlation peak position.

Thus a combined assessment of the plurality of attributes may be used as a basis for selecting the at least one parameter of the ultrasonic measurement signal.

The ultrasonic measurement signal may be set to a minimum peak side lobe (MPS) coded ultrasonic signal if the quality attributes of at least one signal of the set of cross-correlated signals is above a predetermined value.

Thus the ultrasonic measurement signal may be set to a minimum peak side lobe (MPS) coded ultrasonic signal when this type of signal is expected to result in a reliable and robust measurement of the elongation.

The at least one parameter may comprise a measurement base frequency of the ultrasonic measurement signal. The measurement base frequency of the ultrasonic measurement signal may be set to the base frequency of the transmitted primary ultrasonic signal having the highest quality attribute of the set of transmitted primary signals.

Thus the base frequency of the measurement signal may be set in relation to, or even corresponding to, the base frequency of the primary minimum peak side lobe (MPS) coded ultrasonic signal resulting in a high quality attribute.

The method may further comprise:
transmitting a set of secondary minimum peak side lobe (MPS) coded ultrasonic signals with different signal pulse lengths into the fastener,
receiving a corresponding set of reflected secondary ultrasonic signals from the fastener, and
cross-correlating each reflected secondary ultrasonic signal with the corresponding transmitted secondary ultrasonic signal, thus obtaining a set of secondary cross-correlated signals,
determining a quality attribute of each signal of the set of transmitted secondary signals,
determining the pulse length of the ultrasonic measurement signal based on the quality attributes of the set of transmitted secondary signals.

For a certain base frequency, the pulse length of the signal may be determined as a number of periods of the base frequency. The sequence length of the MPS code for coding the signal may thus be selected to correspond to the number of periods of the base frequency.

As previously noted, MPS codes are currently available in sequence lengths (periods of the modulated wave form) up to 68. Barker codes (a type of MPS codes) are known up to sequence lengths of 13. Thus the optimal pulse length of the signal, and the corresponding MPS code may be identified, for performing a measurement.

The quality attribute of each signal of the set of transmitted secondary signals may be based on a cross-correlation peak uniqueness (C) and/or a cross-correlation peak symmetry (D) of the transmitted secondary signals.

When determining a quality attribute of each signal for the selection of pulse length, the cross-correlation peak uniqueness (C) may relate to a ratio of peak height of a main peak to peak height of a secondary peak, e.g. the second most prominent peak in the cross-correlated signal. Thus the uniqueness of the most prominent peak with regard to other correlation peaks may be used as a quality attribute. The cross-correlation peak symmetry (D) may relate to any measurement of symmetry of the main peak, e.g. symmetry of the left hand edge and the right hand edge. Different signal routes in the fastener may result in different time of flight of the signal and thus several correlation peaks. Overlapping correlation peaks may result in asymmetric correlation peaks. By considering cross-correlation peak symmetry the risk of identifying overlapping correlation peaks etc. may be reduced.

The ultrasonic measurement signal may be set to a chirp signal if the quality attributes of each of the set of transmitted primary signals are below a predetermined value.

Thus if, based on the assessment of the quality attributes of the set of transmitted primary signals, no one of the MPS signals is expected to yield a reliable and robust measurement, the ultrasonic measurement signal may be set to a chirp signal. The chirp signal is also a low-autocorrelation signal.

The frequency range of the chirp may be determined by:
transmitting a set of primary ultrasonic chirp signals with different base frequencies into the fastener,
receiving a corresponding set of reflected ultrasonic chirp signals from the fastener, and
determining the frequency range of a measurement chirp signal to comprise the base frequency of the primary chirp signal having the maximum amplitude of the reflected ultrasonic signals.

The frequency range of the chirp may further be determined by defining the range by a lower frequency limit and a higher frequency limit, comprising the base frequency of the primary chirp signal having the maximum amplitude of the reflected ultrasonic signals, and wherein the lower frequency limit and the higher frequency limit are set to frequencies where the reflected ultrasonic signals have an amplitude above a predetermined threshold, e.g. at least 10% of the maximum amplitude of the reflected ultrasonic signals.

Thus the measurement chirp signal may be selected to encompass the range of frequencies where the most reliable and robust measurement may be achieved.

The chirp signal may have a time dependent frequency curve having a rate of change that reflects a frequency response curve of the set of primary ultrasonic chirp signals, defined as the amplitude of the reflected ultrasonic signals as a function of the frequency of the transmitted signals. The rate of change may preferably be inverse to the frequency response curve of the set of primary ultrasonic chirp signals.

Thus the energy used in the chirp measurement signal may be optimised by adjusting the amplitude of individual frequency components in the chirp signal as a function of the amplitude of the reflected ultrasonic signals.

As previously noted, by transmitting minimum peak side lobe (MPS) coded ultrasonic signals into the fastener and cross-correlating reflected and transmitted ultrasonic signals, a much better correlation is achieved when compared to other types of signals, e.g. conventional sine bursts. The correlation between the reflected and transmitted ultrasonic signals may be used to track a phase change of the ultrasonic signal during elongation, e.g. tightening of a threaded fastener. By improving the correlation a measurement of the phase change may be made more reliable and robust. Thus the use of minimum peak side lobe (MPS) coded ultrasonic signals facilitates a more reliable and robust measurement of elongation of a fastener, and the measurement of elongation of a fastener with a power tool may be improved.

The method may further comprise:
cross-correlating the reflected ultrasonic measurement signal with the transmitted ultrasonic measurement signal, thus obtaining a cross-correlated measurement signal,
extracting phase information from the reflected measurement signal, and
determining the elongation of the fastener based on the extracted phase information.

The step of extracting phase information from the reflected measurement signal may comprise using the cross-correlated measurement signal to identify periods of the reflected signal being in phase, and extracting phase information from the periods of the reflected signal being in phase.

The periods of the reflected signal being in phase may be identified by masking the signal with the minimum peak side lobe (MPS) sequence of the transmitted measurement signal.

The step of extracting phase information from the reflected measurement signal may comprise I/Q-modulating the reflected signal and extracting the phase information.

The minimum peak side lobe (MPS) coded ultrasonic signal(s) may be (a) Barker coded or quasi Barker coded ultrasonic signal(s).

Barker coded signals are signals coded according to a Barker sequence. Barker codes are a special case of a minimum peak side lobe (MPS) codes. Barker codes are known for sequences up to 13 periods and have a maximum autocorrelation sequence which has sidelobes lower than a predetermined threshold.

| Length | Known Barker codes | |
|---|---|---|
| 2 | +1 −1 | +1 +1 |
| 3 | +1 +1 −1 | |
| 4 | +1 +1 −1 +1 | +1 +1 +1 −1 |
| 5 | +1 +1 +1 −1 +1 | |
| 7 | +1 +1 +1 −1 −1 +1 −1 | |
| 11 | +1 +1 +1 −1 −1 −1 +1 −1 −1 +1 −1 | |
| 13 | +1 +1 +1 +1 +1 −1 −1 +1 +1 −1 +1 −1 +1 | |

The positive and negative amplitudes (+1 and −1) of the Barker codes imply a biphase modulation, i.e. the change of phase in the carrier wave making up the Barker code is 180 degrees.

Alternatively, the change of phase in the carrier wave may be less than 180 degrees, e.g. 90 degrees, defining a quasi-Barker code.

The modulated waveform may be a sine wave, e.g. a sine burst, thus maintaining phase information in the coded signal. The MPS or Barker coded signal may thus be a sine burst with square envelope, where selected periods of the sine burst are phase shifted according to the MPS or Barker coded carrier wave.

The method may be performed by a power fastening tool, wherein the fastener is a fastener tightened by the power fastening tool.

Thereby, the method of performing a reliable and robust measurement of the elongation of the fastener may be used while tightening the fastener. The method may therefore be used to improve the repeatability in the degree of tightening, e.g. while tightening threaded fasteners.

The invention further relates to a power tool comprising a tool head for engaging with a fastener, an ultrasonic transducer unit for transmitting ultrasonic signals into the fastener and receiving reflected ultrasonic signals from the fastener, and a processing unit connected to the ultrasonic transducer unit, wherein the power tool is configured to:
transmitting a set of primary minimum peak side lobe (MPS) coded ultrasonic signals with different base frequencies into the fastener,
receiving a corresponding set of reflected primary ultrasonic signals from the fastener,
cross-correlating each reflected primary ultrasonic signal with the corresponding transmitted primary ultrasonic signal, thus obtaining a set of primary cross-correlated signals,
determining a quality attribute of each signal of the set of transmitted primary signals,
determining at least one parameter of an ultrasonic measurement signal, for performing measurements of the fastener, based on the quality attributes of the set of transmitted primary signals,
transmitting the ultrasonic measurement signal into the fastener,
receiving a reflected ultrasonic measurement signal from the fastener, and
measuring the elongation of the fastener based on the reflected ultrasonic measurement signal.

Thus the advantages of the method disclosed herein may be achieved by the power tool, obtaining good correlation between transmitted and reflected signals by using minimum peak side lobe (MPS) coded ultrasonic signals, and facilitating a more reliable and robust measurement of elongation of the fastener engaged by the tool head.

The power tool may further configured to perform the method as further disclosed herein, to achieve the advantages disclosed.

The power tool may further be configured to:
cross-correlating the reflected ultrasonic measurement signal with the transmitted ultrasonic measurement signal, thus obtaining a cross-correlated measurement signal,
extracting phase information from the reflected measurement signal and/or from the cross-correlated measurement signal, and
determining the elongation of the fastener based on the phase information.

The power tool may be a power fastening tool, and the fastener may be a fastener tightened by the power fastening tool.

The minimum peak side lobe (MPS) coded ultrasonic signal(s) may be (a) barker coded or quasi barker coded ultrasonic signal(s).

Other features and advantages of the invention will be apparent from the figures and from the detailed description of the shown embodiment.

SHORT DESCRIPTION OF THE DRAWINGS

In the following detailed description reference is made to the accompanying drawings, of which.

DETAILED DESCRIPTION OF THE SHOWN EMBODIMENT OF THE INVENTION

Figure 1:
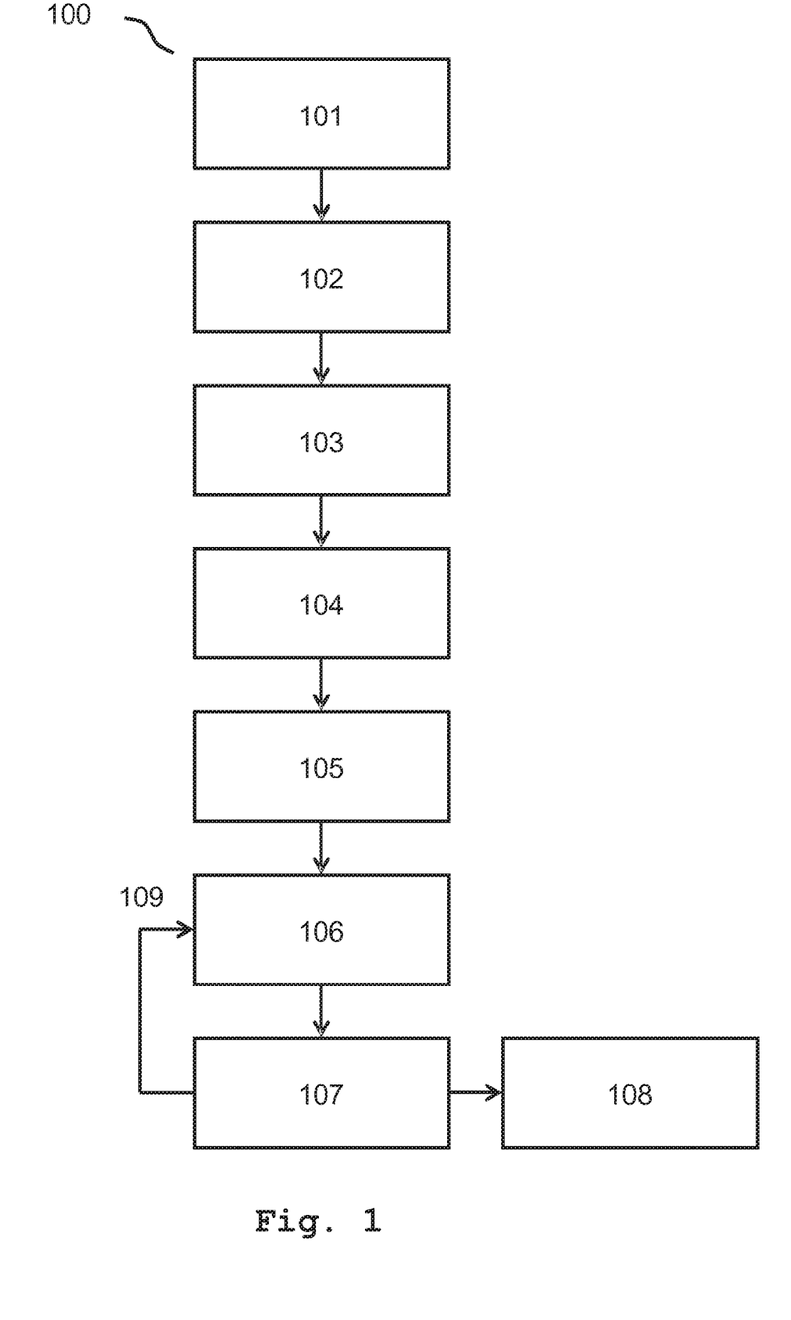
FIG. 1 shows a block diagram of a method of measuring elongation of a fastener with ultrasound, according to one embodiment.

In FIG. 1 a block diagram of a method 100 of measuring elongation of a fastener with ultrasound is shown. The method is performed by a power tool comprising an ultrasonic transducer in acoustic contact with the fastener. The ultrasonic transducer is arranged such that ultrasonic signals may be transmitted into the fastener, and reflected ultrasonic signals may be received by the transducer. Ultrasonic signals may be transmitted and received by one and the same ultrasonic transducer element, or by two or more separate ultrasonic transducer elements. A set of primary minimum peak side lobe (MPS) coded ultrasonic signals with different base frequencies are transmitted, 101, into the fastener. MPS codes are binary sequences with low autocorrelation sidelobe levels. As one case the MPS codes are selected as Barker codes. Barker codes are a special case of MPS codes, which have sidelobes lower than other MPS codes.

To obtain a MPS (or Barker) coded ultrasonic signal, selected periods of an ultrasonic signal to be modulated by a MPS (or Barker) code are phase shifted according to the code. The ultrasonic signal to be modulated may be a sine burst, to maintain phase information in the ultrasonic signal after coding.

As one example, to obtain a Barker coded ultrasonic signal corresponding to a Barker code of length 11, a sine burst having a length of 11 sine periods is phase modulated according to the Barker (length 11) scheme (+1 +1 +1 −1 −1 −1 +1 −1 −1 +1 −1), where +1 indicates positive phase (i.e. no phase modulation) and −1 indicates a phase shift of 180 degrees. Thus the $4^{th}$, $5^{th}$, $6^{th}$, $8^{th}$, $9^{th}$ and $11^{th}$ periods of the sine burst are phase shifted 180 degrees.

The set of primary minimum peak side lobe (MPS) coded ultrasonic signals transmitted into the fastener have different base frequencies, i.e. different periods of the sine wave modulated by the code. The base frequencies of the set of primary minimum peak side lobe (MPS) coded ultrasonic signals may be selected to be in the range of 2-18 MHz.

The transmitted signals are reflected in the fastener, and thereafter a corresponding set of reflected primary ultrasonic signals is received, 102, from the fastener by the ultrasonic transducer of the power tool. The time of flight of the ultrasonic signals indicates the length of the fastener. Typically, the reflected primary ultrasonic signal is received by the power tool before the next primary ultrasonic signal is transmitted into the fastener.

Each reflected primary ultrasonic signal received by the power tool is cross-correlated 103 with the corresponding transmitted primary ultrasonic signal. Thus a set of primary cross-correlated signals is obtained. Each cross-correlated signal relates to the similarity of the received reflected signal and the corresponding transmitted signal.

Figure 2:
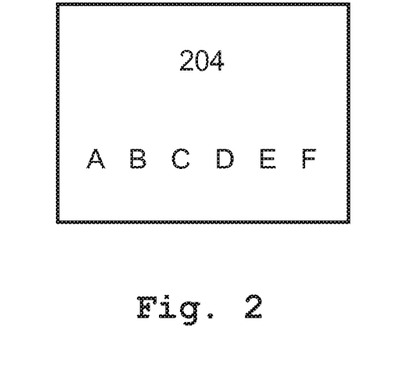
FIG. 2 shows a block diagram of part of a method of measuring elongation of a fastener with ultrasound, according to another embodiment.

From the set of primary cross-correlated signals, a quality attribute is determined 104 for each of the transmitted primary signals. With reference to FIG. 2, the quality attribute of each signal of the set of transmitted primary signals may be based on a weighted sum of attributes selected from A, B, C, D, E and F in the following group:

An amplitude A of the cross-correlated signal. This relates to the total amplitude of the signal. Thus the total amplitude of the signal may be used as a quality attribute, to enhance the signal-to-noise ratio.

A cross-correlation peak height B. This relates to the peak height of the most prominent peak, i.e. a main peak, in the cross-correlated signal. Thus the absolute peak height of the most prominent correlation peak may be used as a quality attribute, to enhance the signal-to-noise ratio.

A cross-correlation peak uniqueness C. Different signal routes in the fastener may result in different time of flight of the signal and thus several correlation peaks. The cross-correlation peak uniqueness may relate to a ratio of peak height of a main peak to peak height of a secondary peak, e.g. the second most prominent peak in the cross-correlated signal. Thus the uniqueness of the most prominent peak with regard to other correlation peaks may be used as a quality attribute.

A cross-correlation peak symmetry D. This may relate to any measurement of symmetry of the main peak of the cross-correlated signal, e.g. symmetry of the left hand edge and the right hand edge. Overlapping correlation peaks corresponding to different signal routes in the fastener may result in asymmetric correlation peaks. By considering cross-correlation peak symmetry the risk of identifying overlapping correlation peaks etc. may be reduced.

An I/Q signal variance E. Thus the method may include an assessment of the quality of a phase extraction from the received signal. If the variation (variance) of the I/Q signal in a given interval is low, the quality of the extracted phase in this interval is high, indicating that the quality of the received signal is high in the interval.

A difference F between reflected signal phase and correlation peak position. The position of the correlation peak may be seen to indicate the time of flight of the signal in a number of periods of the base frequency of the signal. Any deviation from a complete number of periods, i.e. in parts of a period, may indicate a phase shift of the signal. This phase shift may be compared to the reflected signal phase to assess the quality of the signal.

Based on the quality attributes of the set of transmitted primary signals, the base frequency of an ultrasonic measurement signal, for performing measurements of the fastener, may be determined 105. Thus the MPS signal having the highest quality attribute of the set of transmitted primary signals may be selected to perform measurements on the fastener.

Alternatively, if the quality attributes of each of the set of transmitted primary signals are below a predetermined value, the ultrasonic measurement signal may be set to a chirp signal.

Thereafter, the ultrasonic measurement signal is transmitted 106 into the fastener, and a reflected ultrasonic measurement signal is received 107 from the fastener. Based on the transmitted and reflected measurement signal, the elongation of the fastener may be measured 108, as will be described further down with reference to FIG. 7. The elongation is the relative length change of the fastener, i.e. of a fastener during a fastening process.

Further to what is described above, FIG. 3 shows a method 300 of determining pulse length of a MPS coded signal for measuring a fastener. A set of secondary minimum peak side lobe (MPS) coded ultrasonic signals with different signal pulse lengths are transmitted 301 into the fastener. The pulse lengths correspond to the number of periods of the MPS codes that are being used in the method. If the codes are limited to Barker codes, the available sequence lengths are 2, 3, 4, 5, 6, 11 and 13 periods of the modulated signal. For a certain base frequency, the pulse length of the signal may be determined as a number of periods of the base frequency. The sequence length of the MPS code for coding the signal may thus be selected to correspond to the number of periods of the base frequency. As an example, for a base frequency of 11 MHz the Barker 11 code will contain 11 periods of the modulated signal, thus resulting in a pulse length of 1 μs.

Figure 3:
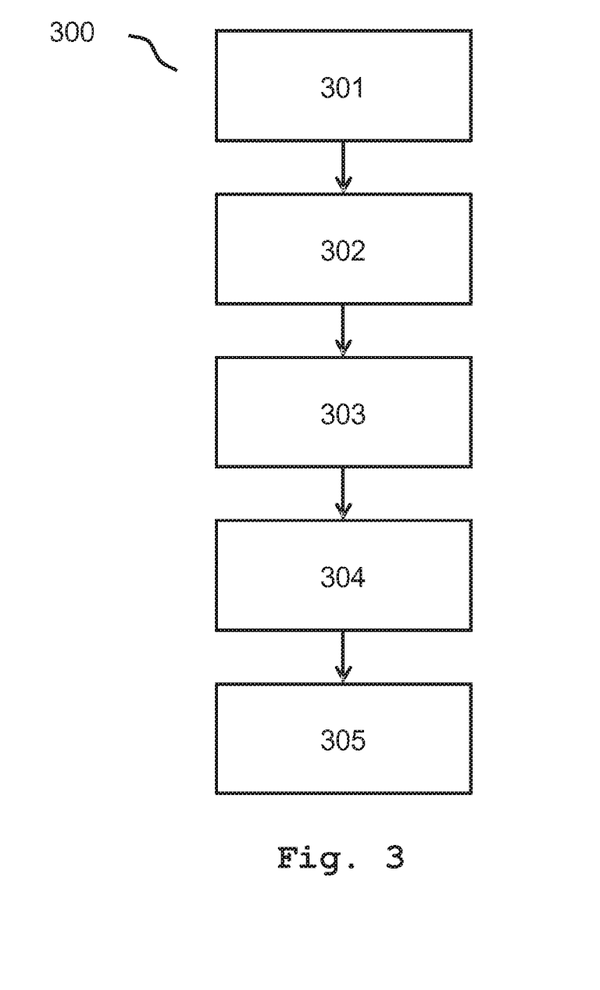
FIG. 3 shows a block diagram of a method of measuring elongation of a fastener with ultrasound, according to yet another embodiment.
Figure 4:
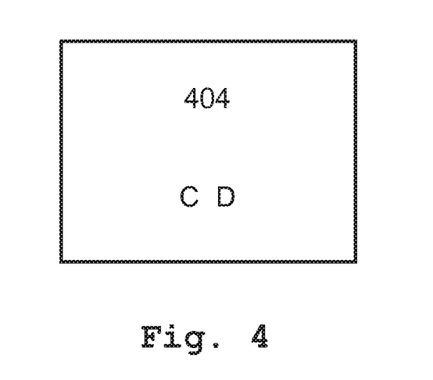
FIG. 4 shows a block diagram of part of a method of measuring elongation of a fastener with ultrasound, according to yet another embodiment.

A corresponding set of reflected secondary ultrasonic signals is received 302 from the fastener. Each reflected secondary ultrasonic signal is cross-correlated 303 with the corresponding transmitted secondary ultrasonic signal, thus obtaining a set of secondary cross-correlated signals. A quality attribute of each signal of the set of transmitted secondary signals is determined 304, and the pulse length of the ultrasonic measurement signal is determined based on the quality attributes of the set of transmitted secondary signals. As illustrated in FIG. 4, the quality attribute of each signal of the set of transmitted secondary signals may be based on a cross-correlation peak uniqueness C and/or a cross-correlation peak symmetry D of the transmitted secondary signals.

Figure 5:
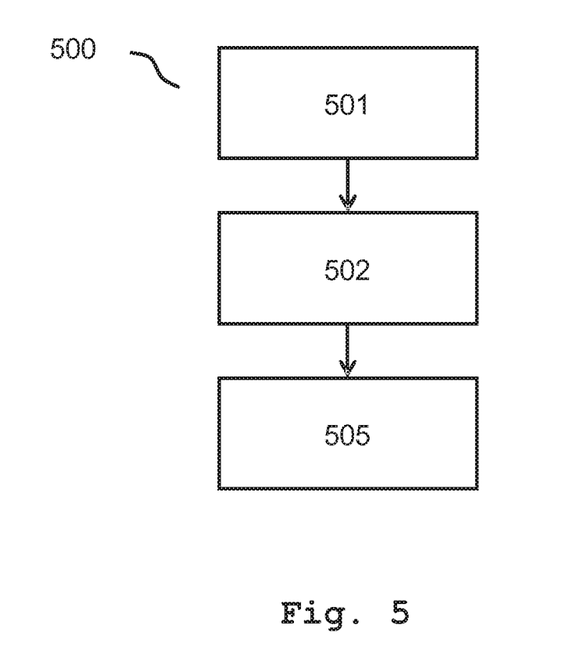
FIG. 5 shows a block diagram of part of a method of measuring elongation of a fastener with ultrasound, according to a further embodiment.

If the measurement signal is selected to a ultrasonic chirp signal in the previous step 105 shown in FIG. 1, the frequency range of the chirp may be determined by the method 500 shown in FIG. 5. A set of primary ultrasonic chirp signals with different base frequencies is transmitted 501 into the fastener by the ultrasonic transducer of the power tool. A corresponding set of reflected ultrasonic chirp signals is received 502 from the fastener, and the frequency range of the measurement chirp signal is determined 505 as the frequency range comprising the base frequency of the primary chirp signal having the maximum amplitude of the reflected ultrasonic signals. The lower frequency limit and the higher frequency limit of the range are set to frequencies where the reflected ultrasonic signals have an amplitude above a predetermined threshold, e.g. at least 10% of the maximum amplitude of the reflected ultrasonic signals. The chirp signal may be configured to have a time dependent frequency curve with a rate of change of frequency that reflects a frequency response curve of the set of primary ultrasonic chirp signals, preferably such that the rate of change is the inverse to the frequency response curve of the set of primary ultrasonic chirp signals.

Figure 6:
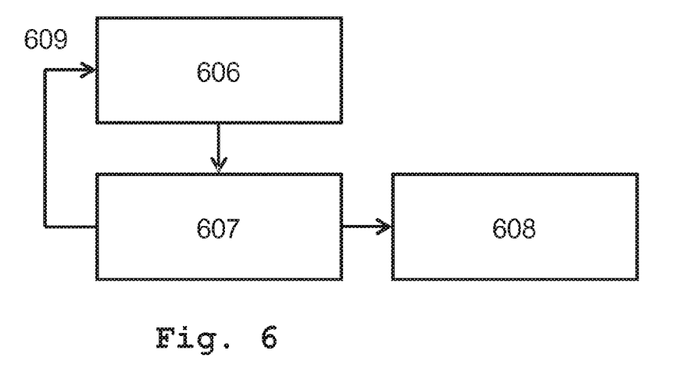
FIG. 6 shows a block diagram of a method of measuring elongation of a fastener with ultrasound, according to yet a further embodiment.

In FIG. 6, a method 600 of measuring elongation of a fastener with ultrasound, performed by a power tool in acoustic contact with the fastener, is shown. A minimum peak side lobe (MPS) coded ultrasonic measurement signal is transmitted 606 into the fastener by the ultrasonic transducer of the power tool. The measurement signal is reflected in the fastener, and a reflected ultrasonic measurement signal is received 607 from the fastener, by the power tool. Based on the reflected ultrasonic measurement signal, the elongation of the fastener is thereafter measured 608. The method may be repeated 609 to monitor changes in elongation of the fastener.

Figure 7:
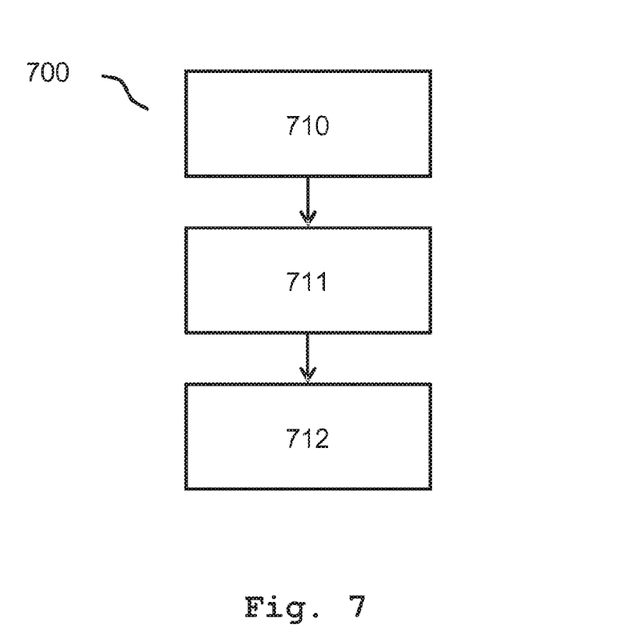
FIG. 7 shows a block diagram of a method of measuring elongation of a fastener with ultrasound, according to still another embodiment.

Changes in the elongation of the fastener may be measured 700 by continuously or periodically performing measurements as above and cross-correlating 710 the reflected ultrasonic measurement signal with the transmitted ultrasonic measurement signal. Phase information may thereafter be extracted 711 from the reflected measurement signal, and the elongation of the fastener may be determined 712 based on the extracted phase information.

To extract phase information from the reflected measurement signal of a MPS signal, the method may comprise using the cross-correlated measurement signal to identify periods of the reflected signal being in phase with the modulated sine signal, and extracting phase information from the periods of the reflected signal being in phase.

The periods of the reflected signal being in phase may be identified by masking the signal with the minimum peak side lobe (MPS) sequence of the transmitted measurement signal.

Phase information may be extracted from the received signal by means of I/Q-modulation (I=in-phase, Q=quadrature), also known as quadrature amplitude modulation.

The signal is then split into an I- and Q-channel and each channel is multiplied with a reference signal. The reference signal of the I-channel is a signal that has the same frequency and that is phase locked to the transmitted signal. The reference signal of the Q-channel corresponds to the I-channel reference signal, but phase shifted 90°. The I- and Q-channels are orthogonal to each other.

The I- and Q-channels are thereafter low pass filtered to generate low pass filtered I- and Q-outputs. From these outputs the phase of the received signal may be extracted by calculating the arc tangent of the I- and Q-output signals.

By the method disclosed the elongation of a fastener drawn by the power tool may be monitored. For as long as the fastener is not subject to any elongation, e.g. prior to a fastening process having actually started, this phase difference between the transmitted and reflected signals will remain constant at some value.

When the fastening process commences this phase difference will increase due to the fact that the elongation of the fastener will result in a longer time of flight of the ultrasonic signal in the fastener. The increasing tension in the fastener also results in a lower speed of sound, thus further increasing the time of flight. By continuously performing measurements as described above, the phase difference between the transmitted and reflected signals may be determined by the power tool. If the total phase difference exceeds a full period, the total number of periods that the echo signal undergoes during a fastening process may be counted. When the phase difference has reached a value corresponding to a desired fastener elongation, which in turn corresponds to a desired tightening force, the tightening process may be interrupted.

The measurement should preferably be repeated at such high repetition frequency (e.g. 1 kHz or higher) during fastening that the phase difference of the reflected signal may be unambiguously determined between successive measurements.

Figure 8:
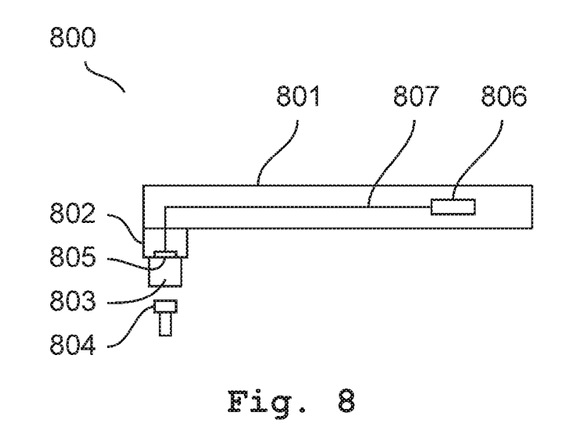
FIG. 8 shows a power tool according to an embodiment.

In FIG. 8, a power tool 800 is shown in the form of an assembly tool. The tool has a tool body 801 to be held by an operator, and a tool head 802 comprising a tool bit 803 for engagement with a fastener in the form of a fastener 804 (e.g. a screw or a nut). During the process of fastening, the tool head and the tool bit is driven in rotation to rotate the fastener. The tool head further supports an ultrasonic transducer unit 805, such that it is in acoustic contact with the fastener. One example of a construction of such an ultrasonic transducer unit arrangement is disclosed in SE 533385. The ultrasonic transducer unit is arranged for transmitting ultrasonic signals into the fastener and receiving reflected ultrasonic signals from the fastener. The tool further comprises a processing unit 806 connected to the ultrasonic transducer unit by electrical connecting means 807. The tool and the processing unit is configured to perform the method as previously described by transmitting a set of primary minimum peak side lobe (MPS) coded ultrasonic signals with different base frequencies into the fastener, receiving a corresponding set of reflected primary ultrasonic signals from the fastener, cross-correlating each reflected primary ultrasonic signal with the corresponding transmitted primary ultrasonic signal, thus obtaining a set of cross-correlated signals, determining a quality attribute of each signal of the set of cross-correlated signals, determining at least one parameter of an ultrasonic measurement signal, for performing measurements of the fastener, based on the quality attributes of the set of cross-correlated signals, transmitting the ultrasonic measurement signal into the fastener, and receiving a reflected ultrasonic measurement signal from the fastener.

The processing unit may be configured to perform the method as described by means of a computer program, which when executed by the processing unit performs the steps of the method.

According to one embodiment the power tool 800 and the processing unit 806 is configured to transmitting a minimum peak side lobe (MPS) coded ultrasonic measurement signal into the fastener, receiving a reflected ultrasonic measurement signal from the fastener, and measuring the elongation of the fastener based on the reflected ultrasonic measurement signal.

The power tool may be adapted to perform any of the steps of the method as disclosed herein. The different steps of the method described above may be combined or performed in any suitable order.

The method may be implemented by a computer program, having code means, which when run in a processing unit causes the processing unit to execute the steps of the method. The computer program may be comprised in a computer readable medium of a computer program product. The computer readable medium may consist of essentially any memory, such as a ROM (Read-Only Memory), a PROM (Programmable Read-Only Memory), an EPROM (Erasable PROM), a Flash memory, an EEPROM (Electrically Erasable PROM), or a hard disk drive.

The power tool and the methods disclosed herein may be modified by those skilled in the art, as compared to the exemplary embodiments described above.

As is obvious for a skilled person, a number of other implementations, modifications, variations and/or additions can be made to the above described exemplary embodiments. It is to be understood that the invention includes all such other implementations, modifications, variations and/or additions which fall within the scope of the claims.

The invention claimed is:

1. A method of measuring elongation of a fastener with ultrasound, performed by a power tool in acoustic contact with the fastener, comprising:
    transmitting a set of primary minimum peak side lobe (MPS) coded ultrasonic signals with different base frequencies into the fastener;
    receiving a corresponding set of reflected primary ultrasonic signals from the fastener;
    cross-correlating each reflected primary ultrasonic signal with the corresponding transmitted primary ultrasonic signal, thus obtaining a set of primary cross-correlated signals;
    determining a quality attribute of each transmitted primary signal from the set of primary cross-correlated signals;
    determining at least one parameter of an ultrasonic measurement signal, for performing measurements of the fastener, based on the quality attributes of the set of transmitted primary signals;
    transmitting the ultrasonic measurement signal into the fastener;
    receiving a reflected ultrasonic measurement signal from the fastener; and
    measuring the elongation of the fastener based on the reflected ultrasonic measurement signal.

2. The method according to claim 1, wherein the quality attribute of each signal of the set of transmitted primary signals is based on attributes selected from the group consisting of an amplitude (A) of the cross-correlated signal, a cross-correlation peak height (B), a cross-correlation peak uniqueness (C), a cross-correlation peak symmetry (D), an I/Q signal variance (E), a difference between reflected signal phase and correlation peak position (F), or combinations thereof.

3. The method according to claim 1, wherein the quality attribute is based on a weighted sum of a plurality of attributes of the respective transmitted primary signals selected from the group consisting of an amplitude (A) of the cross-correlated signal, a cross-correlation peak height (B), a cross-correlation peak uniqueness (C), a cross-correlation peak symmetry (D), an I/Q signal variance (E), a difference between reflected signal phase and correlation peak position (F).

4. The method according to claim 1, wherein the ultrasonic measurement signal is set to a minimum peak side lobe (MPS) coded ultrasonic signal if the quality attributes of at least one signal of the set of transmitted primary signals is above a predetermined value.

5. The method according to claim 4, wherein the at least one parameter comprises a measurement base frequency of the ultrasonic measurement signal.

6. The method according to claim 5, wherein the measurement base frequency of the ultrasonic measurement signal is set to the base frequency of the primary ultrasonic signal having the highest quality attribute of the set of transmitted primary signals.

7. The method according to claim 4, further comprising:
    transmitting a set of secondary minimum peak side lobe (MPS) coded ultrasonic signals with different signal pulse lengths into the fastener;
    receiving a corresponding set of reflected secondary ultrasonic signals from the fastener;
    cross-correlating each reflected secondary ultrasonic signal with the corresponding transmitted secondary ultrasonic signal, thus obtaining a set of secondary cross-correlated signals;

determining a quality attribute of each signal of the set of transmitted secondary signals from the set of cross-correlated signals; and determining the pulse length of the ultrasonic measurement signal based on the quality attributes of the set of transmitted secondary signals.

8. The method according to claim 7, wherein the quality attribute of each signal of the set of transmitted secondary signals is based on a cross-correlation peak uniqueness (C) and/or a cross-correlation peak symmetry (D) of the secondary cross-correlated signals.

9. The method according to claim 8, wherein the ultrasonic measurement signal is set to a chirp signal if the quality attributes of each of the set of transmitted primary signals are below a predetermined value.

10. The method according to claim 9, wherein the frequency range of the chirp is determined by:
    transmitting a set of primary ultrasonic chirp signals with different base frequencies into the fastener;
    receiving a corresponding set of reflected ultrasonic chirp signals from the fastener; and
    determining the frequency range of a measurement chirp signal to comprise the base frequency of the primary chirp signal having the maximum amplitude of the reflected ultrasonic signals.

11. The method according to claim 9, wherein the chirp signal have a time dependent frequency curve having a rate of change that reflects a frequency response curve of the set of primary ultrasonic chirp signals, preferably such that the rate of change is the inverse to the frequency response curve of the set of primary ultrasonic chirp signals.

12. The method according to claim 1, further comprising:
    cross-correlating the reflected ultrasonic measurement signal with the transmitted ultrasonic measurement signal, thus obtaining a cross-correlated measurement signal;
    extracting phase information from the reflected measurement signal and/or from the cross-correlated measurement signal; and
    determining the elongation of the fastener based on the phase information.

13. The method according to claim 12, wherein the step of extracting phase information from the reflected measurement signal comprises using the cross-correlated measurement signal to identify periods of the reflected signal being in phase, and extracting phase information from the periods of the reflected signal being in phase.

14. The method according to claim 13, wherein the periods of the reflected signal being in phase are identified by masking the signal with the minimum peak side lobe (MPS) sequence of the transmitted measurement signal.

15. The method according to claim 1, wherein the step of extracting phase information from the reflected measurement signal comprises I/Q-modulating the reflected signal and extracting the phase information.

16. The method according to claim 1, wherein the minimum peak side lobe (MPS) coded ultrasonic signal(s) is/are (a) Barker coded or quasi Barker coded ultrasonic signal(s).

17. The method according to claim 1, wherein the method is performed by a power fastening tool, and wherein the fastener is a fastener drawn by the power fastening tool.

18. A power tool comprising a tool head for engaging with a fastener, an ultrasonic transducer unit for transmitting ultrasonic signals into the fastener and receiving reflected ultrasonic signals from the fastener, and a processing unit connected to the ultrasonic transducer unit,
    wherein the power tool is configured to:
        transmitting a set of primary minimum peak side lobe (MPS) coded ultrasonic signals with different base frequencies into the fastener;
        receiving a corresponding set of reflected primary ultrasonic signals from the fastener;
        cross-correlating each reflected primary ultrasonic signal with the corresponding transmitted primary ultrasonic signal, thus obtaining a set of cross-correlated signals;
        determining a quality attribute of each signal of the set of cross-correlated signals;
        determining at least one parameter of an ultrasonic measurement signal, for performing measurements of the fastener, based on the quality attributes of the set of cross-correlated signals;
        transmitting the ultrasonic measurement signal into the fastener;
        receiving a reflected ultrasonic measurement signal from the fastener; and
        measuring the elongation of the fastener based on the reflected ultrasonic measurement signal.

19. A power tool, configured to perform the method according to claim 2, comprising a tool head for engaging with a fastener, an ultrasonic transducer unit for transmitting ultrasonic signals into the fastener and receiving reflected ultrasonic signals from the fastener, and a processing unit connected to the ultrasonic transducer unit,
    wherein the power tool is further configured to:
        transmitting a set of primary minimum peak side lobe (MPS) coded ultrasonic signals with different base frequencies into the fastener;
        receiving a corresponding set of reflected primary ultrasonic signals from the fastener;
        cross-correlating each reflected primary ultrasonic signal with the corresponding transmitted primary ultrasonic signal, thus obtaining a set of cross-correlated signals;
        determining a quality attribute of each signal of the set of cross-correlated signals;
        determining at least one parameter of an ultrasonic measurement signal, for performing measurements of the fastener, based on the quality attributes of the set of cross-correlated signals;
        transmitting the ultrasonic measurement signal into the fastener;
        receiving a reflected ultrasonic measurement signal from the fastener; and
        measuring the elongation of the fastener based on the reflected ultrasonic measurement signal.

20. The power tool according to claim 19, further configured to:
    cross-correlating the reflected ultrasonic measurement signal with the transmitted ultrasonic measurement signal, thus obtaining a cross-correlated measurement signal;
    extracting phase and information from the reflected measurement signal and/or from the cross-correlated measurement signal; and
    determining the elongation of the fastener based on the phase information.

* * * * *